United States Patent
Lorenz et al.

(10) Patent No.: US 9,803,091 B2
(45) Date of Patent: Oct. 31, 2017

(54) CROSS-LINKED PLASTIC MATERIAL WITH AN INTRINSIC ANTIMICROBIAL EFFECT BASED ON VINYL ESTERS AND VINYL ESTER URETHANES

(71) Applicant: FACHHOCHSCHULE MÜNSTER, Steinfurt (DE)

(72) Inventors: Reinhard Lorenz, Steinfurt (DE); Björn Fischer, Saerbeck (DE)

(73) Assignee: Fachhochschule Münster, Steinfurt (DE)

( * ) Notice: Subject to any disclaimer, the term of this patent is extended or adjusted under 35 U.S.C. 154(b) by 0 days.

(21) Appl. No.: 14/764,634

(22) PCT Filed: Jan. 31, 2014

(86) PCT No.: PCT/EP2014/051876
§ 371 (c)(1),
(2) Date: Jul. 30, 2015

(87) PCT Pub. No.: WO2014/118312
PCT Pub. Date: Aug. 7, 2014

(65) Prior Publication Data
US 2015/0361277 A1    Dec. 17, 2015

(30) Foreign Application Priority Data
Jan. 31, 2013    (EP) ..................... 13000470

(51) Int. Cl.
| | |
|---|---|
| C09D 5/14 | (2006.01) |
| C07C 209/68 | (2006.01) |
| C07C 211/27 | (2006.01) |
| C08G 18/32 | (2006.01) |
| C08G 18/67 | (2006.01) |
| C08G 18/76 | (2006.01) |
| C09D 139/02 | (2006.01) |

(52) U.S. Cl.
CPC .............. *C09D 5/14* (2013.01); *C07C 209/68* (2013.01); *C07C 211/27* (2013.01); *C08G 18/3275* (2013.01); *C08G 18/672* (2013.01); *C08G 18/7657* (2013.01); *C09D 139/02* (2013.01)

(58) Field of Classification Search
CPC ...... C09D 5/14; C09D 139/02; C07C 209/68; C07C 211/27; C08G 18/3275; C08G 18/672; C08G 18/7657
USPC .......................................... 524/850
See application file for complete search history.

(56) References Cited

U.S. PATENT DOCUMENTS

| | | | |
|---|---|---|---|
| 4,021,416 A | 5/1977 | Locatell, Jr. | |
| 4,447,580 A * | 5/1984 | Ai ........................ | C09D 5/4407 524/517 |
| 4,810,567 A | 3/1989 | Calcaterra et al. | |
| 5,614,568 A | 3/1997 | Mawatari et al. | |
| 6,200,680 B1 | 3/2001 | Takeda et al. | |
| 6,242,526 B1 | 6/2001 | Siddiqui et al. | |
| 6,297,314 B1 | 10/2001 | Hintze-Brüning et al. | |
| 2005/0079150 A1* | 4/2005 | Gellman ................ | A61K 31/74 424/78.27 |
| 2010/0247889 A1 | 9/2010 | Kliesch et al. | |

FOREIGN PATENT DOCUMENTS

| | | |
|---|---|---|
| DE | 44 32 985 A1 | 3/1996 |
| JP | 2000 239 281 A | 9/2000 |
| WO | 2004/033568 A1 | 4/2004 |

OTHER PUBLICATIONS

Ye et al., "Single-step fabrication of non-leaching antibacterial surfaces using vapor crosslinking", J. Mater. Chem., 2011, 21, 257-262.*
Martin et al., "Initiated chemical vapor deposition of antimicrobial polymer coatings", Biomaterials 28 (2007) 909-915.*

* cited by examiner

*Primary Examiner* — Ling Choi
*Assistant Examiner* — Ronald Grinsted
(74) *Attorney, Agent, or Firm* — Jason D. Voight

(57) ABSTRACT

The present invention is directed to a radically curable chemical composition in form of a resin for the production of materials having an intrinsic antimicrobial effect, to the applications of these materials, to a method for the preparation of these resins and materials, and to the use of an amino-functionalized styrene derivative as a reactive diluent. The cross-linked plastic materials formed after curing have an intrinsic antimicrobial effect without the use of additional biocides.

10 Claims, No Drawings

CROSS-LINKED PLASTIC MATERIAL WITH AN INTRINSIC ANTIMICROBIAL EFFECT BASED ON VINYL ESTERS AND VINYL ESTER URETHANES

This is the national stage of International Application PCT/EP2014/051876, filed Jan. 31, 2014.

The present invention is directed to a radically curable chemical composition in form of a resin for the preparation of materials having an intrinsic antimicrobial effect, to the applications of these materials, to a method for the preparation of these resins and materials, and to the use of amino-functionalized styrene derivatives as reactive diluents.

In many applications of plastics and materials the growth of algae, fungi or shells is an unpleasant side effect. However, significantly more serious problems can be caused by the formation of bacterial biofilms and the transmission of pathogens. Combating and preventing these undesirable effects is thus of great medical, hygienic, food technological and practical importance: Common remedies include mechanical and chemical cleaning, the use of conventional biocides (for example silver, copper or zinc compounds, or organic compounds such as triclosan, 10,10'-oxybisphenoxyarsine, N-(trifluoromethylthio)phthalimide, N-(trichloromethylthio)phthalimide, different isothiazoliones) as additives to the plastic or paint, and the continuous use of different external disinfectants, which is a common practice for example in hospitals or in food and meat processing.

Antimicrobial treatment of surfaces has been difficult without the antimicrobial agent used as an additive diffusing out of the surface. There have been some attempts to use antimicrobially functionalized monomers for the synthesis of antimicrobial polymers. One of these monomers was, for example, tert. butylaminoethyl methacrylate (TBAEMA). The disadvantage of the polymers available up to now, such as poly(TBAEMA), was that the glass transition temperature was very low, for example below 50° C. with poly(TBAEMA).

U.S. Pat. No. 6,242,526 describes antimicrobial polymer lattices which are composed of an ethylenically unsaturated acid as an anion and a quaternary ammonium compound as a cation, wherein the antimicrobial effect is attributable to the quaternary ammonium compounds.

U.S. Pat. No. 4,810,567 describes antimicrobial textiles, wherein various base textiles are functionalized by graft copolymerization with monomers containing acid groups to which antimicrobial proteins and antibiotics are bound by amidation.

U.S. Pat. No. 5,614,568 describes an antibacterial, thermoplastic compound which contains, inter alia, silver, copper or zinc zeolites. In addition, polymeric and low-molecular-weight additives with specific functional groups are used, which increase the antimicrobial effect.

U.S. Pat. No. 4,447,580 describes an acrylate-based copolymer containing amino-functionalized styrene monomer units for the preparation of dip paints for cataphoresis. These copolymers are reacted with a thermally activated Michael addition with oligomeric and polymeric compounds which contain activated double bonds. The amino-functionalized styrene derivatives are not used for radical cross-linking, nor for an antimicrobial effect.

JP 2000 239 281 A describes the synthesis of amino-functionalized styrene derivatives, from which cross-linked polymers are prepared that are converted to immobilized polymeric lithium amides. These are used for organic synthesis.

U.S. Pat. No. 6,200,680 describes the preparation of zinc oxide particles using polymeric excipients, including amino-functionalized polymers on the basis of amino-functionalized styrene derivatives.

U.S. Pat. No. 4,021,416 describes aminoethanethiol-functionalized styrene derivatives which can be used as a complexing agent for silver ions and/or soluble silver complexes in photography.

Kuno et al. (Reactive & Functional Polymers 43 (2000) 43-51) describe poly[N-(p-vinylbenzylidene)-tert.-butylamine oxide] as a new radical scavenger for applications in environmental technology.

DE 102 42 561 A1 discloses an antimicrobial coating, wherein the antimicrobial coating comprises polymers of specific cyclic amines having at least one polymerizable unsaturated group. Furthermore, a method for the preparation of these antimicrobial coatings and their use for the preparation of products with antimicrobial properties is described.

DE 44 32 985 A1 discloses binders and their preparation and their use in coating compositions for scratch and acid resistant coatings. The binders are obtained by a radical polymerization of a) (meth)acrylic monomer and optionally another radically polymerizable monomer(s) in the presence of b) cyclic olefin homopolymer and/or cyclic olefin copolymer which are free of olefinic double bonds.

DE 197 23 504 C1 discloses a coating agent, in particular for the coating of plastics, methods for its preparation and its use as a top coat or clear coat.

The coating agents contain
a) one or more specific polyester resins,
b) one or more specific polyacrylate resins,
c) one or more di- and/or polyisocyanates
d) one or more light stabilizers based on a UV absorber
e) one or more specific light stabilizers based on sterically hindered amines, and
f) one or more organic solvents.

In "Schutzschicht gegen Bakterien" [protective layer against bacteria] (Nachrichten aus der Chemie, 59, November 2011, pp. 1039-43) H. Menzel gives an overview of medically appropriate antimicrobial coatings based on polymers with hydrophobic structural elements in combination with a high positive charge density. The different modes of action against gram-positive and gram-negative bacteria are briefly discussed. Most structures are based on quaternary ammonium and phosphonium ions. Antimicrobial polymers for compact material applications are not covered.

The object of the present invention is to provide a technology that can be readily used in practice to produce antimicrobially functionalized surfaces and products in which no antimicrobial additive can diffuse out of the surface or out of the products. Another object is to provide an antimicrobial material that is antimicrobially functionalized "in the bulk", i.e. in its entire volume, and that will therefore when its surface is damaged or modified, for example by impact, abrasion or cutting, form a new surface that is also antimicrobial.

The object underlying the invention is solved in a first embodiment by a resin composition for the preparation of products having an antimicrobial effect containing
a) vinyl ester (VE) and/or vinyl ester urethane (VEU), and
b) styrene derivative as a reactive diluent, wherein preferably for each double bond in component a), there are 0.5 to 8 styrene derivative molecules present in the composition, wherein component b) is amino-functionalized and the amino functionality is of the formula

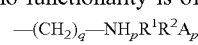

wherein
q is either 1 or 2,
p is 0 or 1,
$R^1$ is selected from H, linear or branched or cyclic alkyl radicals comprising 1 to 10 carbon atoms,
$R^2$ is a linear or branched or cyclic alkyl radical comprising 1 to 10 carbon atoms,
A is the anion of an acid, and
the amine nitrogen N of the above formula is neutrally (p=0) or positively (p=1) charged.

The cross-linked plastic materials formed after curing the VE or VEU resin compositions according to the invention have an intrinsic antimicrobial effect without the use of additional biocides. The new materials are therefore referred to as intrinsically antimicrobial. The advantage of the VE or VEU resin composition according to the invention is that it can be used for the preparation of products from which antimicrobial agents cannot escape and that these products remain antimicrobial even under mechanical modification or damage to their surface.

The composition within the meaning of the invention contains a vinyl ester or vinyl ester urethane and at least one reactive diluent.

It was found that the object underlying the invention could be achieved using radically cross-linked resins of the vinyl ester type (VE resins) and vinyl ester urethane resins (VEU resins). For this purpose, the styrene typically used as a reactive diluent is replaced by an amino-functionalized styrene derivative, a mixture of various amino-functionalized styrene derivatives, a mixture of one or more amino-functionalized styrene derivatives having one or more amino-functionalized methacrylates, or one of these mixtures with further reactive diluents. Further reactive diluents include, for example, styrene, methylstyrene, vinyltoluene, tert. butylstyrene, 4-vinylpyridine, 3-vinylpyridine, 2-vinylpyridine, methyl methacrylate, divinylbenzene, 1,2,4-trivinylcyclohexane, diallyl phthalate, diallyl isophthalate, trisallyl isocyanurate.

In addition, the vinyl ester urethane in the VEU resin may contain amino groups. Furthermore, the antimicrobially treated VE resins and VEU resins according to the patent may be mixed with one another and subsequently cured. According to the invention, mixtures of these intrinsically antimicrobially active resins with intrinsically antimicrobial UP resins are also possible.

Furthermore, mixtures with thermoplastic polymers and intrinsically antimicrobial thermoplastic polymers are also possible according to the invention, for example for impact modification or shrinkage compensation of the thermosets formed. Mixtures of these antimicrobially treated VE and VEU resins with conventional non-antimicrobially treated resins of the UP, VE, VEU and methacrylate type are also possible according to the invention to the extent that the antimicrobial effect is retained.

Vinyl Ester Resin (VE Resin) and Vinyl Ester Urethane Resin (VEU Resin)

The VE resin within the meaning of the invention consists, for example, of the vinyl ester and the reactive diluent. The vinyl esters are, for example, reaction products of bisphenol A-, bisphenol F- and novolak-based glycidyl ethers with methacrylic acid, forming the methacrylic acid ester. Also, glycidyl ethers of other bisphenols (such as bisphenol TMC) may be used. After radical curing (chemical cross-linking), the terms VE thermoset or VE network are used. The bisphenol A-based VE resins are also known as VE/BA resins; the novolak-based resins are known, for example, as VE/NO resins (AVK-TV Guide, "Faserverstärkte Kunststoffe and duroplastische Formassen" [Fibre-reinforced plastics and thermoset moulding materials], $2^{nd}$ edition 2005, page 40).

The VEU resin within the meaning of the invention consists, for example, of the vinyl ester urethane and the reactive diluent. The vinyl ester urethanes are, for example, either reaction products from hydroxypropyl methacrylate and/or hydroxypropyl methacrylate with diisocyanates and/or triisocyanates and/or polyisocyanates. Alternatively, reaction products of diols and/or triols and/or tetrols of different chain lengths, hydroxypropyl methacrylate and/or hydroxyethyl methacrylate and diisocyanates or triisocyanates are used. A suitable selection of diols, triols, tetrols and isocyanates allows, for example, for the cross-linking properties to be tailored to the requirements of very different applications within a wide range. After radical curing (chemical cross-linking), the terms VEU thermoset or VEU network are used. The diols, triols and tetrols used with vinyl ester urethanes are also referred to as chain extenders, regardless of their molar mass.

Preferably, the vinyl ester urethane in component a) may contain amino groups. Especially preferably, the amino groups may be introduced by the use of chain extenders such as bishydroxyethyl methylamine or bishydroxyethyl tert. butylamine. The chain extenders may also be composed of different diols, trials and/or tetraols.

VE resins and VEU resins have substantial structural similarities, which is why according to the invention they belong together: VE and VEU resins carry the radically reactive double bonds, for example in form of a methacrylate function, at the chain end of the oligomeric epoxy or urethane. These epoxies and urethanes may be linear with two chain ends each, trifunctional with three chain ends each, tetrafunctional with four chain ends, and so on. Mixtures may also be used.

Radically reactive double bonds in the molecular chain—as found in unsaturated polyester resins (UP resins)—are generally not present in VE and VEU resins. This has several advantages: After cross-linking, VE thermosets and VEU thermosets show relatively few free chain ends in the network compared to the thermosets of the UP resins. This increases the chemical resistance and the toughness of the network compared to networks of the UP resins. Also, the glass transition of VE and VEU resins is narrower and sharper. Therefore, in the resin producing and resin processing industry, both substance classes are seen as a one. A textbook says, for example: "Vinyl ester resins composed with diisocyanate derivatives form a special group as vinyl ester urethane resins (VEU resins), the moulding materials of which have properties similar to the VE/BA resins and therefore belong to the same type of resin. "(AVK-TV Guide," Faserverstärkte Kunststoffe and duroplastische Formassen", edition 2005, page 40).

The glycidyl ether within the meaning of the invention may also be a mixture of different glycidyl ethers.

Preferably, the vinyl ester in component a) is a vinyl ester of difunctional, trifunctional or higher-functionality glycidyl ether of a divalent, trivalent or higher-valency phenol on the one hand, and methacrylic acid in a molar ratio of 1.25:1 to 0.75:1 on the other.

The vinyl ester urethanes in component a) are preferably either reaction products from hydroxypropyl methacrylate and/or hydroxyethyl methacrylate with diisocyanates and/or triisocyanates and/or polyisocyanates. Alternatively, for example, reaction products of diols and/or triols and/or tetrols of different chain lengths, hydroxypropyl methacrylate and/or hydroxyethyl methacrylate and diisocyanates or triisocyanates are used.

As diisocyanates, monomer MDI, polymer MDI (MDI: methylendiphenyl diisocyanate), 2,4-TDI, 2,6-TDI (TDI: toluylene diisocyanate), IPDI, oligomerization products of the IPDI (IPDI: isophorone diisocyanate), HDI, oligomerization products of the HDI (HDI: hexamethylene diisocyanate) are preferably used, wherein the oligomerization products of the IPDI and the HDI are, for example, the corresponding isocyanurates and biurets that are commercially available in different viscosities and functionalities. In addition, further di- and triisocyanates not belonging to the MDI, TDI, IPDI or HDI group are also suitable according to the invention.

The chain extenders are preferably propylene glycol, dipropylene glycol, tripropylene glycol, oligomeric propylene glycols, polymeric propylene glycols, ethylene glycol, diethylene glycol, triethylene glycol, oligomeric polyethylene oxides, polymeric polyethylene oxides, neopentyl glycol, hydroxypivalic acid neopentylglycol esters, 1,4-butanediol, 1,3-butanediol, 1,2-butanediol, 2,3-butanediol, 1,5-petanediol, 1,6-hexanediol, cyclohexanedimethanol, tricyclodecanedimethanol, isosorbide, bishydroxyethylaniline, bishydroxypropylaniline or any mixtures of these substances.

To prepare the vinyl ester urethanes, preferably a solvent is used, more preferably an aprotic solvent, which may, for example, be acetone or methyl ethyl ketone. Alternatively, a reactive diluent may be used, provided that it does not react with the isocyanate. Therefore, this reactive diluent must preferably have no NH function. Thus, dimethylaminomethylstyrene is, for example, suitable as a solvent, but not tert. butylaminomethylstyrene. For example, a liquid homogeneous mixture of hydroxypropyl and/or hydroxyethyl methacrylate, the one or more chain extenders, a urethanization catalyst and the solvent is prepared, to which the liquid isocyanate (optionally at an elevated temperature) is added dropwise so that a temperature of about 60-80° C. is not exceeded. It may then, for example, be stirred for about 1 hour at 60-80° C. to complete the reaction. Thereafter, the liquid reactive diluent, for example tert. butylaminomethylstyrene, is added and the VEU resin is cooled down to room temperature. If a low-boiling solvent such as acetone or methyl was used, this is distilled off, for example under vacuum.

Reactive Diluent

Within the meaning of the invention, both a single suitable monomer and a suitable monomer mixture may be referred to as a reactive diluent.

The crucial factor is for the monomer or monomer mixture to allow for radical cross-linking and for it to be fully or almost fully integrated into the network.

The composition may, in addition to styrene derivative b), include one or more further reactive diluents from the group of styrene derivatives and/or methacrylates and/or higher-functionality monomers.

Initially, the ratio of double bonds in component a) to styrene derivative molecules is generally not limited. In a preferred embodiment, for each double bond in component a), there are 0.5 to 8, preferably 0.7 to 7, more preferably 1 to 6, even more preferably 1.5 to 4, especially preferably 2.0 to 3.5 styrene derivative molecules present in the composition. If the number is lower, the composition may be too viscous or it may lead to insufficient cross-linking. If the number is higher, the viscosity of the composition may be too low or styrene derivative molecules may not react to completion in the cross-linking reaction and free residual monomer may diffuse out of the product or out of the surface. To prevent this, the residual monomer content should preferably be reduced by longer post-curing at an elevated temperature.

Amino Functionality

The object underlying the invention is achieved in a second embodiment by VE resins or VEU resins for the preparation of products with an antimicrobial effect containing a) a vinyl ester and/or vinyl ester urethane, and
b) styrene derivative, wherein preferably for each double bond in component a), there are 0.5 to 8 styrene derivative molecules present in the composition, wherein the styrene derivative is amino-functionalized, wherein the amino-functionality is of the formula

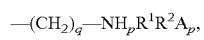

where
q is either 1 or 2,
p is 0 or 1,
$R^1$ is selected from H, linear or branched or cyclic alkyl radicals comprising 1 to 10 carbon atoms,
$R^2$ is a linear or branched or cyclic alkyl radical comprising 1 to 10 carbon atoms,
A is the anion of an acid, and
the amine nitrogen N of the above formula is neutrally (p=0) or positively (p=1) charged.
p may be equal to 1, preferably after neutralization with an acid HA.
$R^2$ of the amino functionality preferably comprises 1 to 10 carbon atoms and is particularly preferably branched, and very particularly preferably selected from isopropyl, tert. butyl or tert. pentyl.
$R^1$ is preferably selected from H or $R^2$.

Provided that $R^2$ has more than three carbon atoms, R1 is preferably selected from H or an alkyl radical having 1 to 3 carbon atoms.

In case component a) is a vinyl ester, the acid may be carbonic acid which is formed in situ in the presence of ambient air or water. In this case, there is a mixture of neutralized and non-neutralized amine. With the amine neutralized in ambient air or in the presence of water, the counter ion A is, for example, especially $HCO_3^-$. A further neutralization results, for example, from reaction with methacrylic acid which has not reacted to completion with the glycidyl ether. In this case, the counter ion is $CH_2\!\!=\!\!C(CH_3)\!\!-\!\!COO^-$. The use of other acids is also possible.

In case component a) is a vinyl ester urethane, the acid may, for example, be carbonic acid which is formed in situ in the presence of ambient air or water. In this case, there is a mixture of neutralized and non-neutralized amine. With the amine neutralized in ambient air or in the presence of water, the counter ion A is mainly $HCO_3^-$. Adding and using other monofunctional or higher-functionality acids is also possible.

As, in general, the styrene monomers easily cross-link the vinyl ester or the vinyl ester urethane in a wide range of compositions, the content of amino-functionalized reactive can be used particularly well to control the content of amino functions in the cross-linked plastic formed.

Vinyl Ester Urethane in Component a)

According to the invention, the vinyl ester urethane may also contain amino groups. Suited to this are, for example, amino diols and triols as well as amino alcohols with an NH structure and an additional tertiary amine. Examples of these chain extenders are: N-methyldiethanolamine, N-tert.

butyldiethanolamine, N-methyldiisopropanolamine, N-tert. butyldiisopropanolamine, 3-(diethylamino)-1,2-propanediol, N-hydroxyethylpiperazine, N,N'-bishydroxyethylpiperazine, N-hydroxypropylpiperazin, N, N'-bishydroxypropylpiperazin, N,N-dimethyl-N',N'-bishydroxyethyl-1,3-diaminopropane, N,N-dimethyl-N',N'-bishydroxyethyl-diaminoethane, triethanolamine, triisopropanolamine.

A further possibility is the use of amino-group-containing polyesterols as chain extenders which are accessible, for example, through the following reaction: Maleic anhydride, maleic acid or fumaric acid are reacted by melt condensation with a stoichiometric excess of a diol, for example ethylene glycol, diethylene glycol, propylene glycol, dipropylene glycol or neopentyl glycol, to obtain a polyester with an acid value of <1 mg KOH/g. The double bonds are reacted quantitatively, or mostly quantitatively, in a subsequent Michael addition with a dialkylamine, for example dimethylamine, diethylamine, diisopropylamine. For this reaction, the dialkylamine is used in stoichiometric excess; after completion of the reaction, the excess of dialkylamine is removed under vacuum. The resulting amino-group-containing polyesterol is terminated with hydroxyl groups and can be used as a chain extender once the OH number has been determined.

Amino-Functionalized Styrene Derivative

In the composition according to the invention, preferably the styrene derivative is amino-functionalized. The molecular weight of the amino-functionalized styrene derivative is preferably in a range of 100 to 300 g/mol, and particularly preferably in a range of 170 to 250 g/mol. It has been found that at an excessively high molecular weight of the monomer, the cross-linking reaction may proceed incompletely.

The amino-functionalized styrene derivative preferably has 10 to 20 carbon atoms, and particularly preferably 12 to 18 carbon atoms.

The functionalized styrene derivative according to the invention is preferably selected from the group of N-(4-ethenylbenzyl)-2-methylpropan-2-amine (also tert. butylstyrene or aminomethyl TBAMS), N-(4-ethenylbenzyl)ethanamine (also ethyl-aminomethyl-styrene or EAMS), N-(4-ethenylbenzyl)propan-1-amine (also n-propyl-aminomethyl-styrene or PAMS), N-(4-ethenylbenzyl)propan-2-amine (also isopropyl-aminomethyl-styrene or IPAMS), N-(4-ethenylbenzyl)butan-1-amine (including n-butyl-aminomethyl-styrene or BAMS), N-(4-ethenylbenzyl)butan-2-amine (also sec. butyl-aminomethyl-styrene or SBAMS), N-(4-ethenylbenzyl)-2-methylpropan-1-amine (also isobutylaminomethyl-styrene or IBAMS), N-(4-ethenylbenzyl)pentan-1-amine (including n-pentyl-aminomethyl-styrene or PENAMS), N-(4-ethenylbenzyl)-3-methylbutan-1-amine (also isopentyl-aminomethyl-styrene or PENAMS I), N-(4-ethenylbenzyl)pentan-3-amine (also 3-pentyl-aminomethyl-styrene or 3-PENAMS), N-(4-ethenylbenzyl)-2-methylbutan-2-amine (also tert. pentyl-aminomethyl-styrene or TPAMS), N-(4-ethenyl benzyl)cyclopentamine (also cyclopentyl-aminomethyl-styrene or CPENAMS), N-(4-ethenylbenzyl)cyclohexanamine (also cyclohexyl-aminomethyl-styrene or CHAMS), N-(4-ethenylbenzyl)-N,N-dimethylamine (also dimethyl-aminomethyl-styrene or DMAMS, N-(4-ethenylbenzyl)-N,N-diethylamine (also diethyl-aminomethyl-styrene or DEAMS), N-(4-ethenylbenzyl)-N-(propan-2-yl)propan-2-amine (also diisopropyl-aminomethyl-styrene or DIPAMS) and mixtures thereof, these compounds being represented as follows:

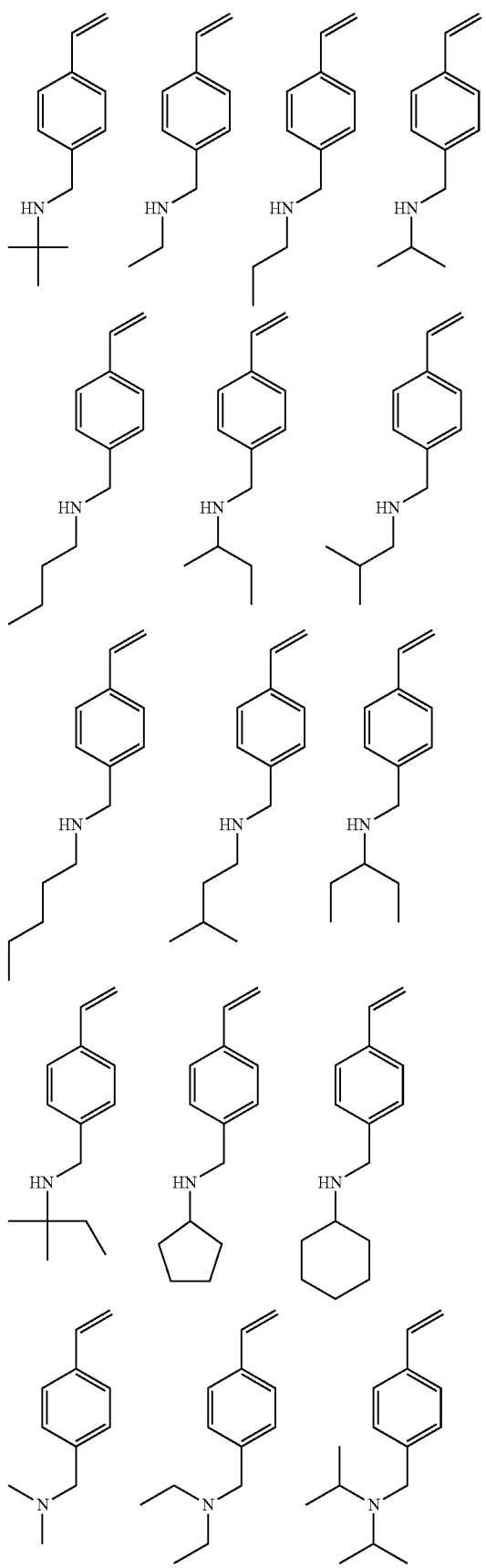

According to the invention, in addition to the aforementioned para isomers, all meta isomers, and all ortho isomers of the aforementioned derivatives and any mixtures of all the ortho, meta and para isomers may be used.

In one embodiment, the object underlying the invention is also achieved by using one or a mixture of these three substances

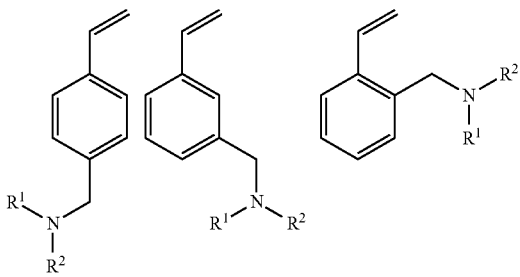

as a reactive diluent,
wherein $R^1$ and/or $R^2$ are independently selected from the group of methyl, ethyl, n-propyl, isopropyl, n-butyl, sec. butyl, isobutyl, tert. butyl, n-pentyl, 3-pentyl, isopentyl, tert. pentyl, cyclopentyl, cyclohexyl,
and wherein $R^1$ may also be H.

In the development of the materials according to the invention, these monomers have been found to be particularly suitable for the production of antimicrobial materials.

Very particularly preferred is the use of the substances with $R^1$ and/or $R^2$ selected from ethyl, isopropyl, tert. butyl, tert. pentyl,
where $R^1$ may also be H.

In a very particularly preferred embodiment, $R^1$ is hydrogen and $R^2$ is selected from isopropyl, tert. butyl, tert. pentyl.

In the present resin composition, for each double bond in component a) there are preferably 0.5 to 8 styrene derivative molecules (component b)). In other words, the ratio of styrene derivative molecules b) to the double bond of component a) is thus 0.5:1 to 8:1. The number of styrene derivative molecules/double bonds in component a) is proportional to the corresponding amounts of substance, so said ratio can also be calculated with the help of these.

The amount of substance of the styrene derivative (component b)) can be determined by the amount used and its molar mass according to $n_{Sty} = m_{Sty}/M_{Sty}$, where $m_{Sty}$ is the amount used and $M_{Sty}$ is the molecular weight of the styrene derivative.

The amount of substance of the double bonds in component a) can be determined by the amount used and the molar mass of component a) according to $n_{Dop} = f \cdot m_{Dop}/M_{Dop}$, where f is the number of double bonds in a molecule of component a), $m_{Dop}$ is the amount used and $M_{Dop}$ is the molecular weight of component a).

Composition

The composition preferably contains at least 20 wt %, particularly preferably at least 50 wt %, and very particularly preferably at least 80 wt % of a mixture of components a) and b). In addition, the composition may, for example, contain other monomers, oligomers, polymers, light stabilizers, initiators, additives, pigments, release agents, rheology additives, fibres and/or fillers.

For every 100 parts by weight of a mixture of components a) and b), there is preferably 0.2 to 4 parts by weight radical initiator present in the composition. This radical initiator is preferably not a peroxide radical initiator. Especially preferably, the radical initiator is a photoinitiator, such as a derivative of the benzoin, the benzil or an α-hydroxyketone or an α-amino ketone or an acylphosphine oxide or a bisacylphosphine oxide. A variety of photoinitiators are known to the skilled person. Photoinitiators that form C radicals are preferred. Especially preferred are C radical generators of the azo initiator type, such as 2,2'-azobis(2-methylpropionitrile), also referred to as AIBN, 1,1-azobis(cyclohexane-1-carbonitrile) or dimethyl-2,2'-azobis(2-methylpropionate) and what is referred to as C—C labile compounds such as 2,3-dimethyl-2,3-diphenylbutane or 3,4-dimethyl-3,4-diphenylhexane.

The radical initiator may also be a mixture of different initiators.

Curing my means of high-energy radiation, for example electron radiation, is also possible.

For every 100 parts by weight of a mixture of components a) and b), there are preferably 20 to 280 parts by weight fillers present in the composition.

For every 100 parts by weight of a mixture of components a) and b), there are preferably 10 to 200 parts by weight glass fibres, carbon fibres, aramid fibres, basalt fibres, natural fibres or textile nonwovens present in the composition.

Further additives such as light stabilizers, shrinkage-reducing thermoplastic polymers, thickeners, release agents, skinning agents and waxes may be used, depending on processing methods and use.

The resin composition according to the invention can, for example, after the addition of additives, fibres and fillers, be used for the production of sheet moulding compounds (SMC), bulk moulding compounds (BMC) and other compounds.

Use of the VE and VEU Resins

In a further embodiment, the object underlying the invention is achieved by applying the resin composition according to the invention in one of the following processing methods:

Coating, painting, pouring, dipping, laminating, gap impregnation, spinning, gluing, resin injection, compression moulding, injection moulding, profile drawing, filling and wrapping.

In a further embodiment, the object underlying the invention is achieved by the use of the VE and VEU resins according to the invention and their compositions according to the invention, for example in the furniture industry, in medicine and in health care, the medical engineering industry, in hospitals, medical practices, retirement homes and rehabilitation centres, in in-home patient care and geriatric nursing care; in the food and meat producing, processing and packaging industry; in the packaging industry, in warehousing and logistics, in the sealing industry, in the livestock and agricultural industries and in domestic animal keeping, in the pharmaceutical industry, in the household goods industry; in apparatus, container and pipeline construction; in the electrical, automotive and construction industries; in the aviation industry, in the textile industry, the sanitary products industry, in the sanitary industry; in the sports, toys and leisure industries; in shipbuilding, in boat building, the water sports industry, ventilation and air conditioning; the public, domestic and industrial water supply and water treatment.

Preparation of Cured Products

In a further embodiment, the object underlying the invention is achieved by a method for the preparation of cured products, wherein the composition according to the invention is cured.

For curing, the temperature is advantageously set to a range of 20 to 200° C.; when photoinitiators are used, lower temperatures are also possible.

Preferably, the cured product, such as a VE or VEU thermoset, is obtained by the method according to the invention for the preparation of cured products. The thermoset consists, for example, of the vinyl ester or vinyl ester urethane and oligomeric bridge structures that have formed from the reactive diluent and that preferably predominantly have an average chain length of 1.5 to 4 monomeric reactive diluent units.

The modulus of elasticity of the VE or VEU thermoset advantageously lies in a range of 2000 to 4000 N/mm². The thermosets advantageously exhibit a strain in a range of 0.5 to 6%. They are preferably odourless.

The cured material can be fibre-reinforced or unreinforced, filled with fillers or unfilled, and may, independently thereof, be used in technical applications of various kinds, in the food industry, in hospitals and in medical devices, in refrigerators, cold stores and many other areas. The antimicrobial behaviour is an intrinsic material property and is not achieved by adding conventional biocides as additives. Thus, the vinyl ester and vinyl ester urethane resin compositions according to the invention and the thermosets and materials obtained therefrom differ significantly from current biocidally treated plastics, which usually operate with nanosilver, isothiazolinones, organic chlorine compounds, triazine derivatives, compounds of copper, tin, zinc and arsenic and other agents. These conventional biocides are controversial due to a (mostly slow) release into the environment, partly poor biodegradability, a heavy metal content, a possible accumulation in individual organisms and/or distribution and spreading through the food chain. With the new intrinsically antimicrobial resins and materials thereof, these disadvantages are reliably avoided.

Product Having an Antimicrobial Effect

In another embodiment, the object underlying the invention is achieved by a product having an antimicrobial effect containing the cured vinyl ester resin or vinyl ester according to the invention.

The product according to the invention consists to more than 20 wt %, preferably more than 50 wt % and particularly preferably more than 80 wt % of the components a) and b).

The product is preferably an adhesive, a sealant, a sealing compound, a coating or a moulding.

In another embodiment, the object underlying the invention is achieved by using the VE or VEU resins according to the invention in the preparation of the following products:

Furniture and furniture coatings, adhesives, veneers and paper laminates, knobs, handles, buttons, switches and housings, panels, floors, pipes, profiles, tanks and containers of all kinds, in particular for drinking water, food and oils, linings of all kinds, roof coatings, light panels, sealants, cements, plugging compounds, polymer concrete, agglomarble, kitchen sinks, shower trays, bathtubs, sinks, toilet seats, garden furniture, garden fences, facade panels, basement window wells, vehicle parts, lights, wind power plants, impregnations, binders, sealing compounds, fillers and/or reaction mortar, coatings, varnishes, gel coats, top coats, ships, boats, recreational items.

Method for the Preparation of the Amino-Functionalized Styrene Derivative

In a further embodiment, the object underlying the invention is achieved by a method for the preparation of an amino-functionalized styrene derivative, wherein
a) in a first step an aqueous alkali hydroxide solution is provided in a concentration ranging from 3 to 7 mol/l (at least the molar equivalent to the amount of substance of haloalkyl styrene),
b) in a second step an amine having at least one hydrogen atom bonded to the nitrogen atom is added to this aqueous alkali hydroxide solution,
c) in a third step a haloalkyl styrene is added in an amount of 0.2 to 0.75 molar equivalents based on the amount of amine,
d) in a fourth step, after all the haloalkyl styrene has been added, the resulting reaction solution is stirred over a period of another 4 to 120 hours, and
e) in a fifth step the amino-functionalized styrene derivative formed is separated out from the rest of the reaction solution.

The haloalkyl styrene is preferably functionalized on the aromatic ring in the ortho and/or meta and/or para position with the haloalkyl group.

Preferably, the aqueous alkali hydroxide solution is provided at a concentration in a range of 4.5-5.5 mol/l. The alkali hydroxide solution is preferably a sodium hydroxide solution. This solution advantageously has a temperature in a range of 20 to 30° C.

The amine is advantageously of the formula $NHR^1R^2$, where $R^1$ is selected from H, linear or branched or cyclic alkyl radicals comprising 1 to 10 carbon atoms, and where $R^2$ is a linear or branched or cyclic alkyl radical comprising 1 to 10 carbon atoms.

Once all the amine has been added, the reaction solution is preferably adjusted to a temperature in a range of 60 to 85° C.

In the haloalkyl styrene, the alkyl group is preferably substituted with only one halogen atom. The alkyl group is preferably methyl. The halogen atom is preferably chlorine.

The haloalkyl styrene is preferably added as a solution in tetrahydrofuran. The concentration of the solution in tetrahydrofuran is preferably in a range of 2 to 3 mol/l. Preferably, the haloalkyl styrene is added dropwise to the current reaction solution, and the reaction solution is preferably stirred for a period of time in a range of 4 to 120 hours. Thereafter, the separation preferably takes place by vacuum distillation.

The subject matter of the present invention also includes a material selected from

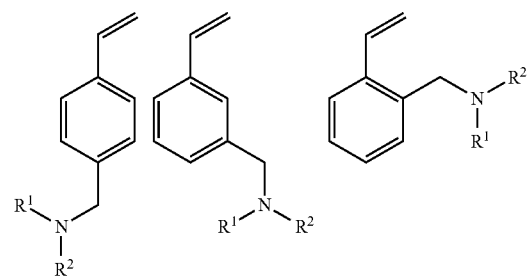

where $R^1$ is hydrogen and $R^2$ is tert. pentyl.

Use of the Amino-Functionalized Styrene Derivative

In another embodiment, the object underlying the invention is achieved by using the amino-functionalized styrene derivative according to the invention for the preparation of antimicrobial coatings or mouldings.

WORKING EXAMPLES

Preparation of the Amino-Functionalized Styrene Derivative (General Procedure)

200 ml of water and 42 g (1.05 mol) NaOH were placed in a 1,000 ml flask and once completely dissolved, they were added to 1.05 mol of the corresponding amine. While stirring, the flask was heated to 60-85° C. and during about 75 minutes, a solution of 53.42 g (0.35 mol) chlorine methylstyrene and 150 ml of THF was added dropwise. Once all of it had been added dropwise, the reaction flask was left in the oil bath for a total reaction period of 4-120 hours under constant stirring. The reaction time and reaction temperature depend on the amine used. The analysis was performed by means of GC-MS. The purification was effected by means of vacuum distillation.

According to this general procedure, amino-functionalized styrene derivatives were synthesized using the following amines: tert. butylamine, n-propylamine, isopropylamine, n-butylamine, sec. butylamine, isobutylamine, n-pentylamine, 3-pentylamine, isopentylamine, tert. pentylamine, cyclopentylamine, cyclohexylamine, diethylamine, diisopropylamine.

The tert. butylaminomethylstyrene obtained with tert. butylamine was abbreviated as TBAMS. It was produced at a reaction temperature of 70° C. and a subsequent stirring time of 24 hours with a conversion of >98% and a selectivity of >98%. In the vacuum distillation, the boiling point of TBAMS 1 was 115° C. at 6 mbar.

Example 1

In a brown glass bottle, 44.26 g (35 wt %) of the bisphenol A-based vinyl ester CRYSTIC VE 671 manufactured by Scott Bader and 82.29 g (65 wt %) of the amino-functionalized reactive diluent TBAMS (tert. butylaminomethylstyrene) were placed on a dolly for 14 days to dissolve, and once completely dissolved, 2 wt % of the azo initiator V601 [2,2'-azobis[dimethyl 2,2'-azobis(2-methylpropionate)] manufactured by Wako was added. Then, about 8 g of the transparent homogeneous resin initiator mixture was placed in each of various glass petri dishes and cured in a nitrogen atmosphere at 70° C. for 2 hours, at 80° C. for 2 hours and at 90° C. for 2 h.

The resulting fully cured VE thermoset was tack-free and hard. The VE thermoset was practically odourless and showed excellent antimicrobial properties.

Example 2

Into a three-necked flask, 0.25 g (600 ppm) of 3,5-di-tert.-butyl-4-hydroxyltoluene (BHT), 0.03 g (60 ppm) of 4-methoxyphenol (HQME), 57.68 g (0.4 mol) of 2-hydroxypropyl methacrylate (HPMA), 32.30 g (0.2 mol) of tert. butyl bis-hydroxyethylamine (TBBHEA) and 84.90 g (20 wt % based on the full VEU resin) of diethylaminomethylstyrene (DEAMS) were measured. The mixture was heated to 65° C. under constant stirring. Once the reaction temperature had been reached, 101.08 g (0.404 mol) of Lupranat MI manufactured by BASF SE (49 wt % of 4,4'-methylene diphenyl diisocyanate, 49 wt % 2,4'-methylene diphenyl diisocyanate, 2 wt % 2,2'-methylene diphenyl diisocyanate) was added dropwise so that the reaction mixture reached a constant temperature between 70° C. and 80° C. The resulting heat was removed via a water bath. Once all had been added dropwise (40 minutes), the mixture was subsequently stirred for 1 hour. Then 148.75 g (35 wt % based on the total VEU resin) of tert. butylaminomethylstyrene (TBAMS) was added and stirred for another 5 minutes.

For curing, 2 wt % of the azo initiator V601 [dimethyl 2,2'-azobis(2-methylpropionate)] manufactured by Wako was added and fully dissolved in the resin. Then about 8 g of the transparent homogeneous resin initiator mixture was placed in each of various glass petri dishes and cured in a nitrogen atmosphere at 70° C. for 2 hours, at 80° C. for 2 hours and at 90° C. for 2 hours.

The resulting fully cured VEU resin thermoset was hard, tack-free, virtually odourless and showed excellent antimicrobial properties.

In this embodiment, the ratio of styrene derivative to double bond is 3.07:1.

Example 3

In a three-necked flask were placed 0.25 g (600 ppm) of 3,5-di-tert.-butyl-4-hydroxyltoluene (BHT), 0.03 g (60 ppm) of 4-methoxyphenol (HQME), 57.68 g (0.4 mol) of 2-hydroxypropyl methacrylate (HPMA), 32.30 g (0.2 mol) of tert. butyl bis-hydroxyethylamine (TBBHEA) and 200 ml of water-free acetone. The mixture was heated to 65° C. under constant stirring. Once the reaction temperature had been reached, 101.08 g (0.404 mol) of Lupranat MI manufactured by BASF SE (49 wt % of 4,4'-methylene diphenyl diisocyanate, 49 wt % 2,4'-methylene diphenyl diisocyanate, 2 wt % 2,2'-methylene diphenyl diisocyanate) was added dropwise so that the reaction mixture reached a constant temperature between 65° C. and 75° C. The resulting heat was removed via a water bath. After all had been added dropwise (25 minutes), the mixture was stirred for 1 hour. Subsequently, the contents of the flask were divided approximately equally between three single-neck flasks weighed empty and an amount of 20.00 g of tert. butylaminomethylstyrene (TBAMS) was placed in each. The acetone was then separated out from all flasks, first at atmospheric pressure and then under vacuum, until a constant total flask mass was reached. After reweighing, the VEU mass present in the each flask was calculated.

Example 3A

Preparation and Curing of the VEU Resin with 65 wt % TBAMS

To the flask containing 66.09 g of VEU and 20.00 g of TBAMS, a further 102.40 g of TBAMS was added to prepare a VEU resin with a total of 65 wt % TBAMS. Subsequently, 2 wt % of the azo initiator V601 [dimethyl 2,2'-azobis(2-methylpropionate)] manufactured by Wako was added and the flask contents were homogenized. About 8 g of the transparent homogeneous resin initiator mixture was placed in each of various glass petri dishes and cured in a nitrogen atmosphere at 70° C. for 2 hours, at 80° C. for 2 hours and at 90° C. for 2 hours.

The resulting fully cured VEU resin thermoset was hard, tack-free, virtually odourless and showed excellent antimicrobial properties.

This embodiment exemplifies how the ratio of styrene derivative to double bond may be calculated.

The vinyl ester urethane (VEU) content corresponds to component a) and amounts to 66.09 g (35 wt %). From example 3 above, one can see that this component a) is obtained from the additive reactions of an equivalent of a chain extender (tert. butyl bis-hydroxyethylamine) with two equivalents of diisocyanate(methylenphenyldiisocyanate) and two equivalents of 2-hydroxypropyl methacrylate, so their molecular weight is 950 g/mol. The VEU component has two vinylic double bonds, so the functionality f equals 2.

This results in $n_{Dop}=f \cdot m_{Dop}/M_{Dop}=2 \cdot 66.09$ g/950 g/mol=0.139 mol The styrene derivative content (tert. butylaminomethylstyrene, TBAMS) corresponds to component b) and amounts to 20+102.4 g=122.4 g (65 wt %). The molecular weight is 189 g/mol.

This results in $n_{Sty}=m_{Sty}/M_{Sty}=122.4$ g/189 g/mol=0.648 mol

The ratio of styrene derivative to double bond is:

$$n_{Sty}:n_{Dop}=0.648 \text{ mol}:0.139 \text{ mol}=4.66:1$$

Example 3B

Preparation and Curing of the VEU Resin with 60 wt % TBAMS

To the flask containing 58.73 g of VEU and 20.00 g of TBAMS, a further 68.10 g of TBAMS was added to produce a VEU resin with a total of 60 wt % TBAMS. Subsequently, 2 wt % of the azo initiator V601 [dimethyl 2,2'-azobis(2-methylpropionate)] manufactured by Wako was added and the flask contents were homogenized. About 8 g of the transparent homogeneous resin initiator mixture was placed in each of various glass petri dishes and cured in a nitrogen atmosphere at 70° C. for 2 hours, at 80° C. for 2 hours and at 90° C. for 2 hours.

The resulting fully cured VEU resin thermoset was hard, tack-free, virtually odourless and showed excellent antimicrobial properties.

In this embodiment, the ratio of styrene derivative to double bond is 3.79:1.

Example 3C

Preparation and Curing of the VEU Resin with 55 wt % TBAMS

To the flask containing 57.43 g of VEU and 20.00 g of TBAMS, a further 50.19 g of TBAMS was added to produce a VEU resin with a total of 55 wt % TBAMS. Subsequently, 2 wt % of the azo initiator V601 [dimethyl 2,2'-azobis(2-methylpropionate)] manufactured by Wako was added and the flask contents were homogenized. About 8 g of the transparent homogeneous resin initiator mixture was placed in each of various glass petri dishes and cured in a nitrogen atmosphere at 70° C. for 2 hours, at 80° C. for 2 hours and at 90° C. for 2 hours.

The resulting fully cured VEU resin thermoset was hard, tack-free, virtually odourless and showed excellent antimicrobial properties.

In this embodiment, the ratio of styrene derivative to double bond is 3.07:1.

Example 4

In a brown glass bottle, 50.00 g (37.6 wt %) of the vinyl esters (1-methylethylidene)bis[4,1-phenyleneoxy(2-hydroxy-3,1-propanediyl)]bismeth-acrylate (corresponds to component a) available from Sigma Aldrich, product number: 494356, M=512.59 g/mol) and 83.09 g (62.4 wt %.%) of the amino-functionalized reactive diluent TBAMS (tert. butylaminomethylstyrene corresponds to component b))

were placed on a dolly for 4 days to dissolve, and once completely dissolved, 2 wt % of the azo initiator V601 [Dimethyl 2,2'-azobis(2-methylpropionate)] manufactured by Wako was added. Then, about 8 g of the transparent homogeneous resin initiator mixture was placed in each of various glass petri dishes and cured in a nitrogen atmosphere at 70° C. for 2 hours, at 80° C. for 2 hours and at 90° C. for 2 h.

The resulting fully cured VE thermoset was tack-free and hard. The VE thermoset was practically odourless and showed excellent antimicrobial properties.

In this embodiment, the ratio of styrene derivative to double bond is 2.26:1.

Procedure Used to Determine Mechanical Behaviour and Glass Transition Temperature To determine the network TG, glass-fibre reinforced thermoset test pieces were produced from the resins and characterized by means of dynamic mechanical analysis (DMA).

Using the DMA 242 manufactured by Netzsch it is possible to determine storage modulus and loss modulus as well as the loss factor of a sample as a function of the temperature, time and frequency of a sinusoidal vibration load applied.

To produce the required test pieces, the resins prepared as per the embodiments, charged with 2 wt % initiator (V601 by Wako), were used.

To this end, three 15×15 cm layers of Saertex® glass fibre non-crimp fabric (biaxial 0°/90°/type: S14EB540-00620-T1300-487000) were impregnated with the respective resin, placed in a 150×150×5 mm screw-down plate mould lined with Mylar® film, and air bubbles were removed as far as possible by brushing down with a spatula. The cavity of the mould was then filled up with more resin, covered with Mylar® film and closed by screwing down the upper mould plate. The curing was carried out for 2 hours at 70, 80 and 90° C., respectively, in a drying cabinet.

After cooling, the GRP panels were cut with a table saw and, where necessary, brought to the required sample size with a sanding belt.

Parameters and measurement settings in the DMA analyses performed:
Sample Size: 50×10×5 mm
Deformation mode: Dual cantilever
Amplitude: 30 μm
Dynamic force: 7.55 N
Static force: 4 N
Temperature range: 20-160° C.
Heating range: 2 K/min
Frequency: 1 Hz/10 Hz
Atmosphere: N2
Flow rate N2: 5 ml/min
Procedure Used for Antimicrobial Testing The method applied is based on the Japanese JIS Z 2801:2000 standard. The test microorganism used in the experiments was the pathogenic germ *Staphylococcus aureus*. Rather than a multiresistant strain, a standard strain (ATCC 6538) was used.

With each test germ (here *Staphylococcus aureus*), a microorganism-specific germ content was determined under the production conditions of the starting solution or starting suspension. With *Staphylococcus aureus*, this value was 108 germs per ml (see also remarks below).

Antimicrobial activity was determined by comparing the growth of *Staphylococcus aureus* on reference surfaces to that on the sample materials.

Empty petri dishes were used as reference material. The samples consisted of petri dishes into each of which a thin layer of a polymer sample had been poured. In each test series, three reference plates were used to determine the initial germ content (separate experiment independent of the antimicrobial behaviour test) as well as three reference plates and three sample plates to determine the surface germ content after incubation.

All plates were inoculated with 400 µl of *Staphylococcus aureus* inoculum that was set to a germ content of 4.0-10*$10^5$ CFU/ml.

The inoculum applied was covered with a sterile PP film in order to avoid evaporation. Immediately after the inoculation, the three sample plates and three reference plates were placed in an incubation cabinet and incubated for 2 hours and 24 hours, respectively, at 35° C. and 90% humidity.

To determine the germ content of the inoculation solution (initial germ content), three reference plates were washed immediately after inoculation by placing 10 ml of SCDLP bouillon (soy casein peptone bouillon with lecithin and polyoxyethylene medium) in the petri dish. The film was flipped using sterile tweezers and repeatedly flooded and flushed using a 1 ml pipette. The petri dish was waved in a figure eight before pipetting 1 ml of the rinsing solution into the first dilution level. Once a thinning series had been set up, the living germ content was determined using the drop plate method. The drop plate method entailed applying—in duplicate—5 drops of 10 µl each onto a plate count (PC) agar plate in every sector of the dilution level. The plates were incubated for 2 hours and 24 hours, respectively, at 37° C.

The rinsing and determination of the living germ count on the reference and test plates after the incubation was performed applying the procedure followed to determine the initial germ content. As regards the test plates, besides raising the detection limit, the germ content of the direct rinsing solution was determined using the pour plate method. To this end—also in duplicate—1 ml of the solution was placed in an empty petri dish, over which liquid PC agar, tempered at 45° C., was poured. By waving it in a figure eight, the bacteria were distributed in the agar. The plates were incubated for 48 hours at 37° C.

After the incubation, the colonies in the petri dish were counted. It was assumed that each germ had turned into a visible colony. After the incubation, the colonies could be discerned by the naked eye. If necessary, a light table could be used to make the germs more visible.

Based on the volume of the inoculation solution and the thinning ratios applied, one could deduce the living germ count of the microorganisms per volumetric unit (i.e. per ml) of inoculation solution. The calculation was performed based on a weighted arithmetic average, applying the following formula:

$$\bar{c} = \frac{\sum c}{n_1 \cdot 1 + n_2 \cdot 0.1} \cdot d$$

where $\bar{c}$ represents the weighted arithmetic average $\Sigma c$ represents the sum of the colonies of all petri dishes or sectors used as a basis for the calculation, $n_1$ represents the number of the petri dishes or sectors of the lowest evaluable dilution level, $n_2$ represents the number of petri dishes or sectors of the next higher dilution level, and d represents the lowest evaluated dilution level.

When using the pour plate method, petri dishes with up to 300 CFU could be counted. When using the drop plate method, only plates with up to 150 CFU per sector could be counted.

The thinning factor F1 had to be maintained when determining the living germ count per ml. This was the sum of the volume of the SCDLP bouillon and the volume of the bacterial suspension on the inoculated plate divided by the volume of the bacterial suspension on this inoculated plate.

$$F_1 = \frac{10 \text{ ml} + 0.4 \text{ ml}}{0.4 \text{ ml}} = 26$$

$F_1$ represents the thinning factor of the SCDLP bouillon.

This resulted in the following formula, which was applied to determine the total germ count on the inoculated sample or reference plates using the pour plate method:

$$CFU = \frac{\sum c}{n_1 \cdot 1 + n_2 \cdot 0.1} \cdot d \cdot F_1$$

When using the drop plate method, a further thinning factor became relevant, as a quarter of a plate was only inoculated with 50 µl, i.e. 0.05 ml. To deduce the germ content per ml, 0.05 ml had to be scaled up to 1 ml by multiplying it by 20.

$$F_2 = 26 \cdot 20$$

$F_2$ represents the thinning factor used to obtain the CFU in the drop plate method per ml.

Accordingly, the total germ count of the inoculated sample and reference plates was calculated for the drop plate method taking account of all thinning factors applying the following formula:

$$CFU = \frac{\sum c}{n_1 \cdot 1 + n_2 \cdot 0.1} \cdot d \cdot F_2$$

To calculate antimicrobial activity, in every test series, the individual results of the living germ count for the plates were combined to form a simple arithmetic mean, based on which the $\log_{10}$ reduction between the sample and reference plates was determined.

The calculation was performed by applying the following formula:

$$\log_{10}\text{-Reduction} = \log_{10}(KG)_{Ref(x)} - \log_{10}(KG)_{Pr(x)}$$

where $(KG)_{Ref(x)}$ represents the CFU on the reference plates at time instance x $(KG)_{Pr(x)}$ represents the CFU on the sample plates at time instance x According to JIS Z 2801:2000, antimicrobial activity exists if the log reduction is at least 2.0 after 24 hours of exposure.

If there are no countable colonies on the agar plates of the samples at the lowest dilution level using the pour plate method, the result was stated as <10 CFU/ml, in line with the requirement in the test standard.

Results of the Mechanical and Antimicrobial Tests

| Example | Composition VE or VEU | Reactive diluent (mass fraction) | $T_G$ at 1 Hz | $T_G$ at 10 Hz | Initial germ content (log CFU/ml) | Reference germ content after 24 h (log CFU/ml) | Surface germ content of sample after 24 h (log CFU/ml) | Log reduction |
|---|---|---|---|---|---|---|---|---|
| 1 | Crystic VE 671 (Scott Bader) | TBAMS (0.65) | 104.3 | 111.5 | 5.6 | 7.5 | 1.1 | 6.4 |
| 2 | HPMA$_{0.4}$TBBHEA$_{0.2}$Lupranant MI$_{0.404}$ | DEAMS (0.2)/ TBAMS (0.35) | 106.7 | 114.8 | 5.3 | 8.4 | 2.7 | 5.7 |
| 3A | HPMA$_{0.4}$TBBHEA$_{0.2}$Lupranant MI$_{0.404}$ | TBAMS (0.65) | 97.6 | 106.4 | 5.3 | 8.4 | 1 | 7.4 |
| 3B | HPMA$_{0.4}$TBBHEA$_{0.2}$Lupranant MI$_{0.404}$ | TBAMS (0.60) | 102.6 | 111.2 | 5.3 | 8.4 | 3.1 | 5.3 |
| 3C | HPMA$_{0.4}$TBBHEA$_{0.2}$Lupranant MI$_{0.404}$ | TBAMS (0.55) | 100.5 | 109.1 | 5.3 | 8.4 | 2.4 | 6.0 |
| 4 | (1-Methylethylidene)bis-[4,1-phenyleneoxy(2-hydroxy-3,1-propanediyl)]bis methacrylate | TBAMS (0.62) | 110.3 | 117.5 | 5.7 | 7.8 | 1.5 | 6.3 |

The invention claimed is:

1. A resin composition for the preparation of products having an antimicrobial effect, containing
   a) vinyl ester and/or vinyl ester urethane, and
   b) styrene derivative as a reactive diluent,
   wherein for each double bond in component a) there are 0.5 to 8 styrene derivative molecules present in the composition,
   wherein component b) is amino-functionalized and the amino functionality is of the formula

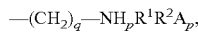

wherein
   q is either 1 or 2,
   p is 0 or 1,
   $R^1$ is selected from H, linear or branched or cyclic alkyl radicals comprising 1 to 10 carbon atoms,
   $R^2$ is a linear or branched or cyclic alkyl radical comprising 1 to 10 carbon atoms,
   A is the anion of an acid, and
   the amine nitrogen N of the above formula is neutrally (p=0) or positively (p=1) charged,
   wherein the amino-functionalized styrene derivative is selected from the group consisting of

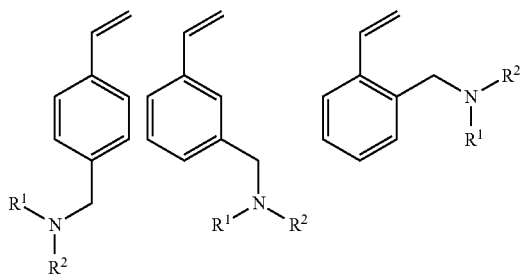

and mixtures thereof,
   wherein R1 is hydrogen and
   R2 is selected from the group consisting of isopropyl, tert-butyl and tert-pentyl.

2. A composition according to claim 1, wherein the vinyl ester urethane contains amino-group-containing chain extenders.

3. A composition according to claim 1, wherein said composition contains at least 20 wt % of a mixture of components a) and b).

4. A composition according to claim 1, wherein for each double bond in component a) there are 1.5 to 4 styrene derivative molecules present in the composition.

5. A method of coating, painting, pouring, dipping, laminating, gap impregnation, spinning, gluing, resin injection, compression moulding, injection moulding, profile drawing, filling or wrapping, said method comprising curing the composition of claim 1.

6. A method for the preparation of cured products, wherein a composition according to claim 1 is cured.

7. A product having an antimicrobial effect including a cured composition according to claim 6.

8. The product according to claim 7 selected from the following products: furniture and furniture coatings, adhesives, veneers and paper laminates, knobs, handles, buttons, switches and housings, panels, floors, pipes, profiles, tanks and containers for drinking water, food and oils, linings, roof coatings, light panels, sealants, cements, plugging compounds, polymer concrete, agglomarble, kitchen sinks, shower trays, bathtubs, sinks, toilet seats, garden furniture, garden fences, facade panels, basement window wells, vehicle parts, lights, wind power plants, impregnations, binders, sealing compounds, fillers and/or reaction mortar, coatings, varnishes, gel coats, top coats, ships, boats or recreational items.

9. The composition of claim 1 wherein $R^2$ is tert-pentyl.

10. A composition according to claim 1, wherein said composition contains at least 80 wt % of a mixture of components a) and b).

* * * * *